United States Patent [19]

Forsythe et al.

[11] 3,972,116

[45] Aug. 3, 1976

[54] SHEAR

[75] Inventors: Alan K. Forsythe; Charles J. Green, both of Vashon, Wash.

[73] Assignee: Hazleton Laboratories Corporation, Vienna, Va.

[22] Filed: Feb. 14, 1975

[21] Appl. No.: 550,019

[52] U.S. Cl. .................................. 30/228; 30/92; 83/198; 128/92 R
[51] Int. Cl.² .................. B23D 15/14; B26B 15/00
[58] Field of Search ............ 30/180, 228, 233, 241, 30/242, 243, 92, 226; 83/198; 128/92 R

[56] References Cited
UNITED STATES PATENTS

| 65,557 | 6/1867 | Flinn | 30/241 X |
|---|---|---|---|
| 1,901,067 | 3/1933 | Vickers | 83/198 |
| 3,495,330 | 2/1970 | Bruce | 30/228 X |
| 3,624,720 | 11/1971 | Laky | 83/198 |
| 3,670,411 | 6/1972 | Peters | 30/228 X |

Primary Examiner—Al Lawrence Smith
Assistant Examiner—J. C. Peters
Attorney, Agent, or Firm—Christensen, O'Connor, Garrison & Havelka

[57] ABSTRACT

A pin shear for shaping and cutting bone pins and other elongate elements to the desired length is described. A pneumatically operated, coaxial cutter assembly includes a cutter plug having pin passageways therethrough positioned inside a cutter body having an aperture therein located in registry with the passageway in a first position. The cutter plug is adapted to move within the cutter body to a second position out of registry with the aperture, whereby an elongate element positioned in the passageway and aperture is severed. A pneumatic operator including means for multiplication of the force applied is described.

12 Claims, 7 Drawing Figures

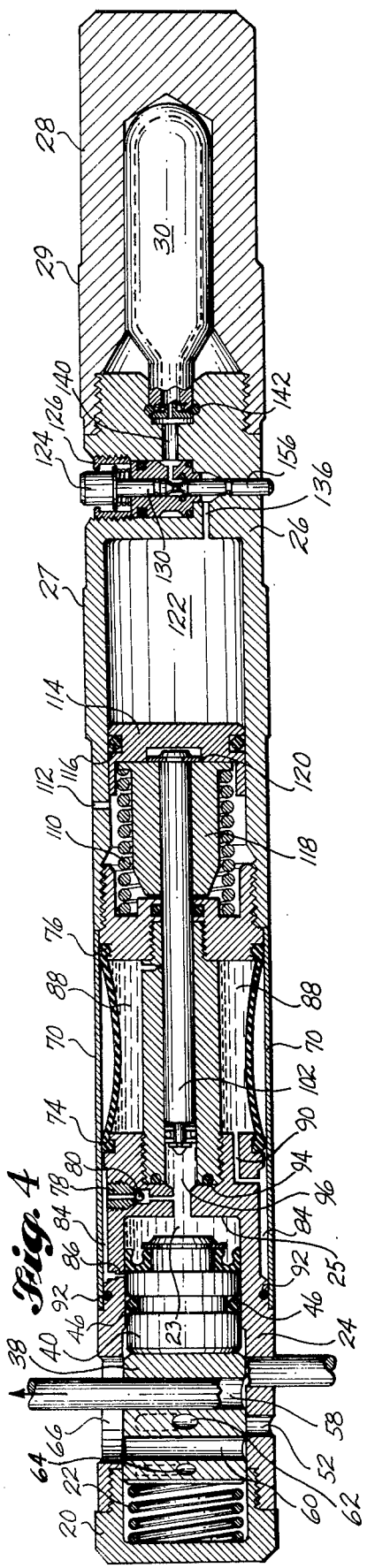

SHEAR

BACKGROUND OF THE INVENTION

This invention relates to means for severing bone pins or other elongate elements transversely without imposing twisting, racking or other forces upon the element during severing.

Heretofore, devices for shearing bone pins and other cylindrical elements have included saws, pinch-type and coaxial, manually operated shears and the like which are satisfactory for usage in some instances with the smaller diameter bone pins, but become difficult to use with the larger diameter, intramedullary bone pins frequently being used in the fixation of fractures of large bones in both the human and veterinary orthopedic medicine fields. In addition, many of the prior art devices twist, rack and otherwise distort the element being severed and frequently leave a jagged and distorted end after severing. To accommodate the various sizes of pins in use, it is necessary to have a plurality of the prior art instruments for cutting the pins to the desired length. In addition, in instances in which one end of the bone pin has already been anchored in the intramedullary zone of a bone, the prior art devices pose difficulties in holding the bone pin during severing.

One well-known prior art device comprises a rotatable pin cutter means positioned within a cutter body. The cutter body and cutter plug means are rotated by movement of handles attached to each element of the cutter. A pin is placed into a diametric passageway in the cutter plug which is aligned with an aperture in the cutter body. The elements are then manually rotated with respect to each other, severing the pin. The requirement of long handles attached to the cutter elements in order to develop sufficient force for cutting the pin makes this device cumbersome and under certain circumstances unusable when severing a bone pin positioned in the bone of a large animal. A substantial amount of working space is necessary for using this device, making it difficult to use in cutting pins in some positions.

OBJECTS OF THE INVENTION

It is therefore an object of this invention to provide a conveniently usable bone pin apparatus for severing bone pins in the medical and veterinary orthopedic sciences.

It is a further object of this invention to provide a bone pin shear which will accommodate a plurality of standard size bone pins.

It is a still further object of this invention to provide a shear for transversely cutting elongated elements without racking or twisting the elements.

It is another object of this invention to provide a bone pin shear with a hydraulic force multiplication means therein which permits repeated severing of bone pins.

One specific object of this invention is to provide a bone pin shear which may be utilized in cutting a bone pin which may have one end thereof inserted into the bone at or near a fracture site to cut the pin to the desired length with a relatively smooth end.

SUMMARY OF THE DISCLOSURE

As herein disclosed, the improved pin shear comprises a generally interfitting cutter assembly having a first cutter body with at least one cutter aperture therein surrounding a cutter plug means having a pin passageway therethrough, the passageway being in alignment with the aperture in a first position and out of registry with the aperture in a second position. The cutter body encloses the cutter plug to provide a close interfit between the members whereby a cylindrical element placed in the pin passageway and aperture in the first position is severed by movement of the cutter plug to the second position. The relative movement of the cutter plug and cutter body is induced by a pneumatically operated, force inducing mechanism which may include means for force multiplication, such as a small diameter slave piston driven by the large diameter pneumatic piston which in turn actuates a larger diameter hydraulic piston. Alternatively, mechanical force multiplication devices may be utilized.

In a preferred embodiment a small gas cylinder is utilized to provide the pneumatic operating fluid. A three-way valve means permits alternate pressurization of the force applying pneumatic operator and depressurization thereof to the atmosphere. A means to increase the force applied to the cutter means provides sufficient force to sever bone pins inserted into the cutter.

The force multiplication and pneumatic operator means may be utilized to operate other types of shear means either in conjunction with the above-described, coaxial shear means or separate therefrom. For example, a nipper-type cutter may be added to the structure so that bone pins may be cut immediately adjacent the surrounding flesh or bone after emplacement of the pin into the bone. The configuration of the passageways through the cutter body may be formed so that pins can be bent therein either before or after severing so that pins shaped to meet the needs of the particular orthopedic task may be formed.

These and other objects and advantages of the invention will become more apparent from a reading of the description of the applicants' preferred embodiment set forth below and from an examination of the appended drawings.

IN THE DRAWINGS

FIG. 4 is a view similar to FIG. 3 after activation of the pneumatic control and consequent cutting of the bone pin.

FIG. 5 is a cross-sectional view of the apparatus taken along lines 5—5 of FIG. 3.

FIG. 6 is an enlarged, sectional view of the control valve used in this invention.

FIG. 7 is a view similar to FIG. 6 wherein the control means has been activated, permitting flow of gases under pressure to the apparatus.

DETAILED DESCRIPTION OF THE PREFERRED EMBODIMENT

Refer now specifically to the drawings, showing the preferred embodiment, wherein like numerals indicate like parts.

Figure 1:
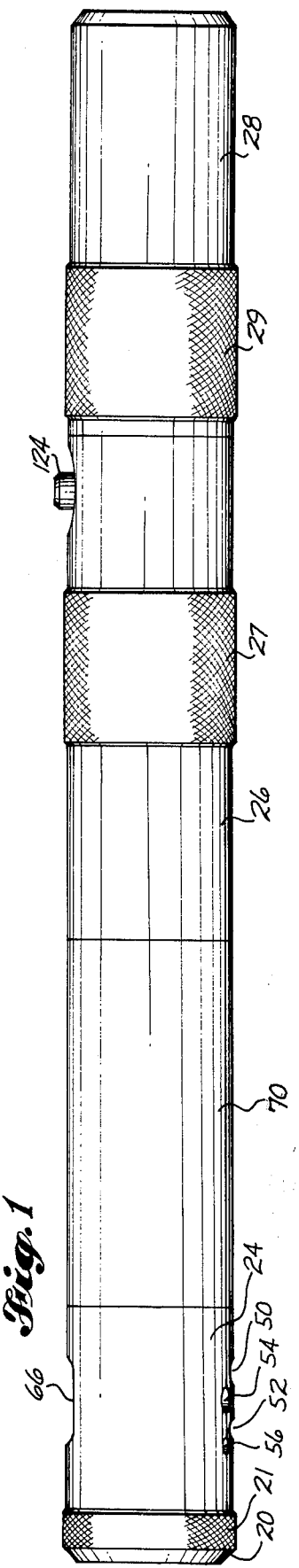
FIG. 1 is a side elevational view of the apparatus of this invention.
Figure 2:
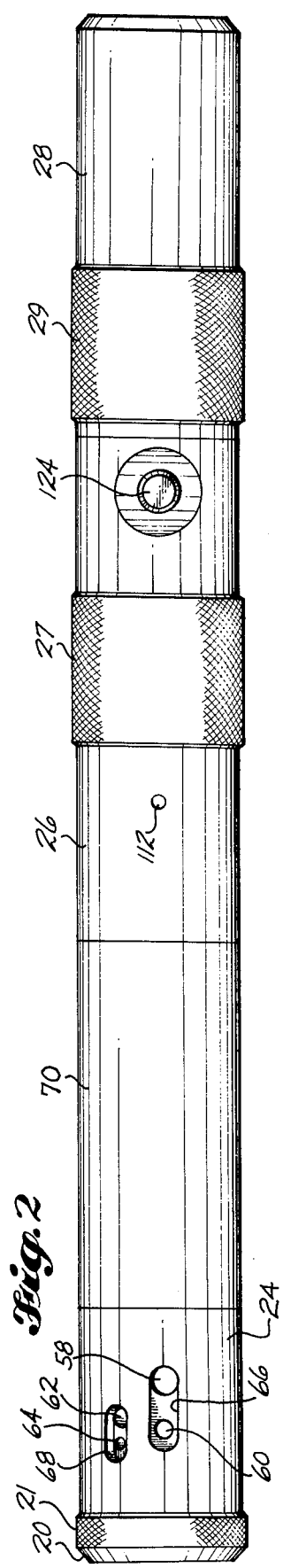
FIG. 2 is a plan view of the apparatus of this invention.
Figure 3:
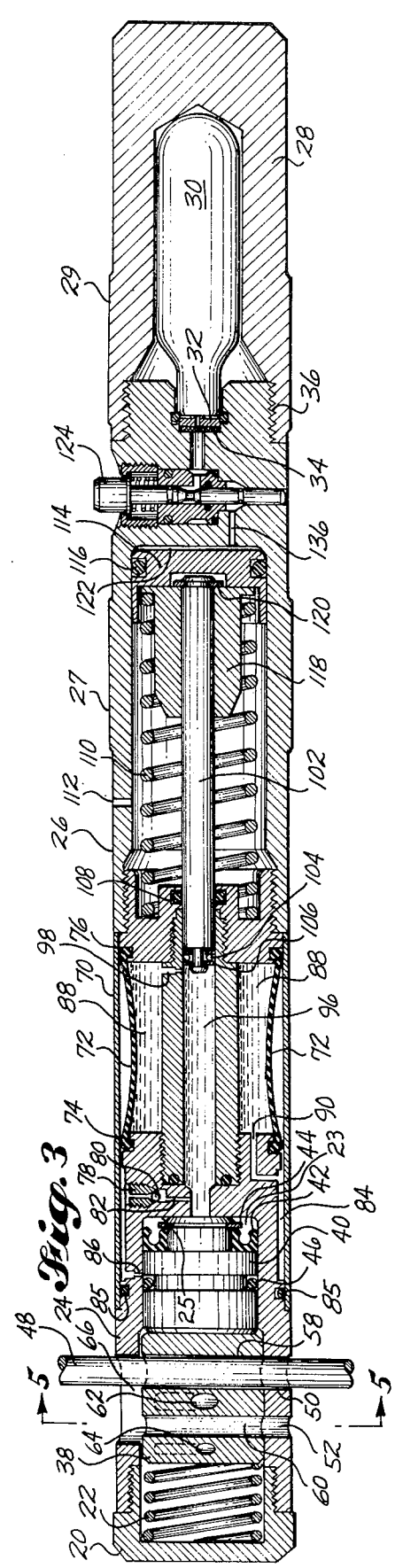
FIG. 3 is a side elevational view of the apparatus shown in FIG. 1 in cross-section, the section being taken axially through the apparatus.

The bone pin shear has a cylindrical shape with a control plunger shown generally at 124 protruding therefrom and a plurality of apertures 50, 52, 54 and 56 through which bone pins or other cylindrical elements of various sizes may be inserted for severing. With specific reference to FIGS. 3–7, the cylindrical body has an end cap 20 affixed to a hydraulic body 24 by means of screw threads or other suitable fasteners. The end cap 20 engages and compresses spring 22 which in turn urges cutter plug 38 and piston 40 away from end cap 20 and into its first or inactivated position against wall 25 of hydraulic chamber 24. Cutter plug 38 is designed to reciprocate axially under forces imposed by a pneumatically actuated force multiplying system described at length below. Reciprocation of cutter plug 38 with a cylindrical element, such as bone pin 48, inserted through passageway 58 results in severing of the bone pin at the interface between passageway 58 and aperture 50. For smaller diameter bone pins, the shear apertures 52, 54 or 56 with their corresponding cutter plug passageways 60, 62 and 64 would be utilized. For severing other elongate elements having other than a cylindrical shape, the shear aperture discussed above may be utilized; however, a square aperture or a shear means adapted to fit the specific cross-section of the elongate element being severed may be utilized. For example, in the well-known "Kirschner-type" bone pin, a fluted exterior surface is utilized. In order to cut such pins conveniently, the shear apertures may be modified to substantially interface with the surface of the particular element being severed. Similarly, the passageways through cutter 38 may have a configuration which substantially receives the elongate element in an interfitting relationship. The cutter plug 38 has at the end opposite the apertures a power piston means 40 for delivering power to the cutter plug. This piston is hydraulically operated and utilizes power seal 42 to develop a seal with the interior of hydraulic body 24. To prevent leakage of the hydraulic fluid, an O-ring 46 is shown adjacent the power seal 42 with a small hydraulic return duct 86 provided so that any leakage past power seal 42 will be returned to the outer reservoir 84. The main fluid reservoir 88 and the outer fluid reservoir 84 are interconnected by duct 90 for free flow of hydraulic fluid therebetween.

Slave piston 102 operates in chamber 96 to provide the fluid pressure necessary for operation of the power piston 40 and in turn the cutter plug means 38. Reciprocation of slave piston 102 increases the hydraulic fluid pressure in chamber 96 causing reciprocation of the piston 40 and cutter plug 38. In the event that cutter plug 38 does not completely sever the bone pin 48 on an initial stroke, and cutter plug 38 remains in a forward position, hydraulic fluid may be drawn into chamber 96 via duct 82 through ball valve 80 as the slave piston is withdrawn. This ball valve 80 is provided for the purposes of make-up of hydraulic fluid in the chamber 96 and prevents back flow of the fluid therefrom under pressurization. The ball valve 80 operates against the check valve plug 78 for uni-directional flow of hydraulic fluid into chamber 96. Duct 98 is provided as shown so that slave piston 102 may be withdrawn without requiring cutter plug 38 to assume the position shown in FIG. 3, but rather to remain in its advanced position until a second or third pressurization is accomplished for cutting a particularly difficult elongate element. At that time, the excess hydraulic fluid in chamber 96 is returned to oil reservoir 88 via duct 98.

The oil reservoir 88 is bounded on its periphery by a substantially annular diaphragm means 72 provided so that the volume of hydraulic fluid in reservoir 88 may vary without creating pressure or vacuum therein. The diaphragm 72 has seal means 74 and 76 at each end thereof to prevent leakage of hydraulic fluid to the outside diaphragm 72 from outer reservoir 84. Similarly, an O-ring 85 seals the forward end of outer fluid reservoir 84. An O-ring seal 108 is provided to prevent leakage of hydraulic fluid back from the chamber 96 past the pressure producing O-ring 104 and its retainer 106. Slave piston 102 is connected directly to spacer 118 which in turn engages pneumatic piston 114. Spacer 118 is urged against pneumatic piston 114 by spring 110 and serves to withdraw slave piston 102 from chamber 96 due to the presence of snap ring 120. The pneumatic piston 114 is positioned for reciprocation within pneumatic chamber 122. A pneumatic seal is obtained by usage of O-ring 116. A vent 112 permits air or other gases trapped in the vicinity of spring 110 to be exhausted to the atmosphere. Pneumatic chamber 122 is supplied with gas under pressure from pressure reservoir 30 via a three-way valve, the structure of which will be described more completely below.

Referring more particularly to FIGS. 6 and 7, the structure and operation of the valve mechanism utilized in this invention will be apparent. Gas under pressure from cylinder 30 enters gas supply duct 140 through piercing disk 32 and filter 34 and enters plenum 138 through plenum duct 144 in valve core 130.

The three-way valve mechanism used in this invention includes a plunger 124 positioned for reciprocation within valve core 130. The plunger 124 is held in its position by retainer 126 and is urged upwardly against shoulder 127 of retainer 126 by spring 128. Retainer 126 is shown threaded into pneumatic body 26, but may be fastened therein by other means such as soldering or the like. Plunger 124 has along its length an O-ring seal 150, a reduced diameter valve section 152, and a second O-ring 154 near the tailpiece 156 thereof. The valve core 130 is sealed into its position by means of O-rings 132 and 134. Interior O-ring 160 is situated on the interior of valve core 130 and O-ring 150 situated on the plunger 124 provide the seals necessary for maintaining pressure within plenum 138 while the valve is in the position shown in FIG. 6. In FIG. 6, as will be noted by the arrows, gas is free to exhaust from chamber 122 past O-ring 154 and along the tailpiece 156 of the plunger 124 to the atmosphere. When plunger 124 is moved to the position shown in FIG. 7, the O-ring 154 first engages the bore of pneumatic body 26 to form a seal preventing further flow of gas outwardly past tailpiece 156 to the atmosphere. Shortly thereafter, along the translation of valve plunger 124, the seal between O-ring 160 and plunger 124 is broken so that gas under pressure in plenum 138 is free to pass alongside the plunger 124 and into gas duct 136 to pressurize chamber 122. Thus, full pressure of the gas supply source 30 is imposed upon chamber 122 when the valve means is in the position shown in FIG. 7. Upon release of pressure upon the end of plunger 124, the spring 128 urges plunger 124 into the position shown in FIG. 6, and the pressurized gas in chamber 122 is permitted to exhaust to the atmosphere as discussed above.

In FIG. 5, the various locations of the cutter apertures and cutter plug passageways are shown. Shear aperture 52 and its corresponding cutter plug passageway 60 are shown as is the bone pin 48 placed within cutter plug passageway 58 and shear aperture 50. Key 39 acts to keep the cutter plug 38 in the proper angular relationship with hydraulic body 24.

Operation of the Preferred Embodiment

In operation a pressurized gas cylinder 30 is placed into the handle 28 and the seal thereof pierced by forcing the cutter element of disk 32 into the seal at the neck of cylinder 30. The bone pin 48 is placed into the shear aperture and cutter plug passageway corresponding to its diameter and positioned so that the interface between cutter plug 38 and the shear aperture, in this case shear aperture 50, is located at the position at which the bone pin is to be cut. The valve is opened by depressing plunger 124 to the position shown in FIGS. 4 and 7, causing flow of pressurized gas into chamber 122. The gas under pressure causes piston 114 to travel to the location shown in FIG. 4, thereby pressurizing the hydraulic fluid in chamber 96 which in turn causes reciprocation of the cutter plug as shown. The bone pin 48 is severed and the device is removed from the pin. The pressure on plunger 124 is released and it returns to the position shown in FIGS. 3 and 6, permitting the pressurized gas in chamber 122 to flow out to the atmosphere. Piston 114 then retracts under influence of spring 110 withdrawing slave piston 102 to the position shown in FIG. 3. The pressure in chamber 96 is thus relieved and cutter plug 38 is urged to return to the position shown in FIG. 3 by spring 22.

In addition to the cutter mechanism described at length above, the applicants' device may embody other types of cutters such as opposed, sharpened surfaces or nippers which are operated by the pneumatic operator through the force multiplication means described. It is also contemplated that means for bending the rods and for performing other functions which may be necessary to shape and sever cylindrical elements may be performed with the applicants' device. By providing a curved or otherwise distorted passageway through the cutter plug, cylindrical elements may be shaped and bent to the desired configuration for use in orthopedics or other applications.

While the applicants have shown and described their present best embodiment of this invention, it will be apparent to one skilled in the art that this invention may take variant forms while remaining within the scope and spirit of the appended claims. For example, mechanical force multiplication apparatus may be utilized in place of the hydraulic system shown and described above. The motion of the cutter plugs may be translated into rotary motion instead of reciprocation by known devices. Other sources of pneumatic pressure may be utilized and other modifications well-known to those skilled in the art taken in view of the applicants' teachings herein.

We claim:

1. A pin shear for cutting bone pins and other elongate objects, said pin shear comprising:
    an elongated housing including a cutter plug chamber, a hydraulic chamber, a pneumatic chamber, and a pneumatic source chamber in end-to-end relationship in that order extending from one end of said elongated housing to the other end thereof, said elongated housing including at least one aperture allowing access to said cutter plug chamber in a direction transverse to the longitudinal axis of said elongated housing;
    a cutter plug means slideably mounted in said cutter plug chamber so as to be movable along the longitudinal axis of said elongated housing between first and second positions, said cutter plug means including at least one aperture extending along an axis transverse to the axis of movement of said cutter plug means, said at least one aperture of said cutter plug means being aligned with said at least one aperture in said elongated housing when said cutter plug means is in said first position and said at least one aperture in said cutter plug means being nonaligned with said at least one aperture in said elongated housing when said cutter plug means is in said second position;
    a power piston means mounted in said hydraulic chamber so as to be movable along the longitudinal axis of said elongated housing, one end of said power piston means adapted to apply force to said cutter plug means in a manner such that said power piston means when moved towards said cutter plug chamber causes said cutter plug means to move from said first position to said second position;
    hydraulic fluid contained in said hydraulic chamber on the side of said power piston means remote from said cutter plug chamber;
    a pneumatic piston means mounted in said pneumatic chamber so as to be movable along the longitudinal axis of said elongated housing, said pneumatic piston means including a pneumatic piston and a slave piston, said slave piston mounted for movement into said hydraulic chamber when said pneumatic piston is moved toward said power piston means; and,
    a valve mounted in said elongated housing between said pneumatic source chamber and said pneumatic chamber so as to control the flow of gas from said pneumatic source chamber into said pneumatic chamber, said flow causing said pneumatic piston to move said slave rod into said hydraulic chamber and thereby apply hydraulic pressure to said power piston means, said hydraulic pressure causing said power piston means to move said cutter plug means from said first position to said second position.

2. A pin shear for cutting bone pins and other elongate objects as claimed in claim 1 wherein said hydraulic chamber is generally cylindrical in shape and includes a large diameter section and a contiguous small diameter section, said power piston means being movably mounted in said large diameter section and said slave piston being movable into said small diameter section.

3. A pin shear for cutting bone pins and other elongate objects as claimed in claim 2 including:
    a hydraulic reservoir surrounding said hydraulic chamber;
    a first passageway adapted to allow hydraulic fluid to move between said hydraulic reservoir and said small diameter section of said hydraulic chamber when said slave piston is withdrawn from said small diameter section to a predetermined position; and,
    a second passageway adapted to allow hydraulic fluid to flow between said hydraulic reservoir and said hydraulic chamber as said slave piston is withdrawn from said small diameter section of said hydraulic chamber.

4. A pin shear for cutting bone pins and other elongate objects as claimed in claim 3 including a one-way valve mounted in said second passageway.

5. A pin shear for cutting bone pins and other elongate objects as claimed in claim 4 including a first return spring means mounted so as to create a force that opposes said hydraulic pressure and assists in returning said cutter plug means to said first position when said slave piston is withdrawn from said small diameter section of said hydraulic chamber.

6. A pin shear for cutting bone pins and other elongate objects as claimed in claim 5 including a second return spring means for creating a force adapted to withdraw said slave piston from said hydraulic chamber.

7. A pin shear for cutting bone pins and other elongate objects as claimed in claim 6 wherein:
   said slave piston is operatively associated with and extends coaxially outwardly from said pneumatic piston; and,
   said slave piston and said pneumatic piston are both cylindrical with the diameter of said pneumatic piston being substantially larger than the diameter of said slave piston.

8. A pin shear for cutting bone pins and other elongate objects as claimed in claim 7 wherein said valve is movable between two positions, said first position allowing gas from said pneumatic source chamber to flow into said pneumatic chamber and said second position allowing gas to be evacuated from said pneumatic chamber while preventing gas from flowing from said pneumatic source chamber to said pneumatic chamber.

9. A pin shear for cutting bone pins and other elongate objects as claimed in claim 1 including a return spring means mounted so as to create a force opposing the force created by said hydraulic pressure, said opposing force tending to move said cutter plug means to said first position.

10. A pin shear for cutting bone pins and other elongate objects as claimed in claim 1 including a return spring means for creating a force adapted to withdraw said slave piston from said hydraulic chamber.

11. A pin shear for cutting bone pins and other elongate objects as claimed in claim 10 wherein:
    said slave piston is operatively associated with and extends coaxially outwardly from said pneumatic piston; and,
    said slave piston and said pneumatic piston are both cylindrical with the diameter of said pneumatic piston being substantially larger than the diameter of said slave piston.

12. A pin shear for cutting bone pins and other elongate objects as claimed in claim 1 wherein said valve is movable between two positions, said first position allowing gas from said pneumatic source chamber to flow into said pneumatic chamber and said second position allowing gas to be evacuated from said pneumatic chamber while preventing gas from flowing from said pneumatic source chamber to said pneumatic chamber.

* * * * *